(12) United States Patent
De Zolt et al.

(10) Patent No.: US 11,097,068 B2
(45) Date of Patent: Aug. 24, 2021

(54) SAFETY NEEDLE WITH DEFORMABLE CANNULA FOR INJECTOR PEN

(71) Applicant: SOL-MILLENNIUM SWISS R&D CENTER SA, Lugano (CH)

(72) Inventors: Dario De Zolt, Fagnano Olona (IT); Matteo Lagana, Longone al Segrino (IT)

(73) Assignee: SOL-MILLENNIUM SWISS R&D CENTER SA, Lugano (CH)

(*) Notice: Subject to any disclaimer, the term of this patent is extended or adjusted under 35 U.S.C. 154(b) by 155 days.

(21) Appl. No.: 16/613,224

(22) PCT Filed: May 29, 2018

(86) PCT No.: PCT/IB2018/053812
§ 371 (c)(1),
(2) Date: Nov. 13, 2019

(87) PCT Pub. No.: WO2018/220529
PCT Pub. Date: Dec. 6, 2018

(65) Prior Publication Data
US 2020/0139054 A1    May 7, 2020

(30) Foreign Application Priority Data
May 30, 2017   (IT) .................. 102017000059104

(51) Int. Cl.
*A61M 5/32*   (2006.01)
*A61M 5/50*   (2006.01)

(52) U.S. Cl.
CPC ........ *A61M 5/3272* (2013.01); *A61M 5/3204* (2013.01); *A61M 5/326* (2013.01);
(Continued)

(58) Field of Classification Search
CPC .. A61M 5/3272; A61M 5/3204; A61M 5/326; A61M 5/3286; A61M 5/5086;
(Continued)

(56) References Cited

U.S. PATENT DOCUMENTS

2002/0068909 A1   6/2002   Alchas et al.
2012/0022461 A1   1/2012   Schubert et al.
(Continued)

FOREIGN PATENT DOCUMENTS

GB           2532795 A    6/2016

OTHER PUBLICATIONS

International Search Report and Written Opinion for Corresponding International Application No. PCT/IB2018/053812 (10 Pages) (dated Aug. 13, 2018).

*Primary Examiner* — Theodore J Stigell
*Assistant Examiner* — Rachel T. Smith
(74) *Attorney, Agent, or Firm* — Lucas & Mercanti, LLP

(57) ABSTRACT

A safety needle having a rigid outer structure within which there is a cannula holding element of being movably coupled to an injector pen for a drug is provided. The cannula holding element supports a cannula having a first extremity and a second extremity for administration of the drug. A moving protective element associated with the rigid structure, covers the second extremity of the cannula after administration, with provision being made for a deforming member capable of deforming the cannula after administration of the drug so that the second extremity of the cannula remains within the protective element. The deforming member is associated with the protective element and is capable of rotating autonomously with respect thereto after administration of the drug to deform the cannula.

9 Claims, 7 Drawing Sheets

(52) U.S. Cl.
CPC ........ *A61M 5/3286* (2013.01); *A61M 5/5086* (2013.01); *A61M 2005/3249* (2013.01); *A61M 2005/3267* (2013.01)

(58) Field of Classification Search
CPC .. A61M 2005/3249; A61M 2005/3267; A61M 2005/325; A61M 2005/3282; A61M 2005/3284; A61M 5/3243; A61M 5/50; A61M 5/3202
See application file for complete search history.

(56) References Cited

U.S. PATENT DOCUMENTS

2014/0221924 A1\* 8/2014 Hiles ................... A61M 5/3221
604/110
2016/0121055 A1 5/2016 Zhang et al.

\* cited by examiner

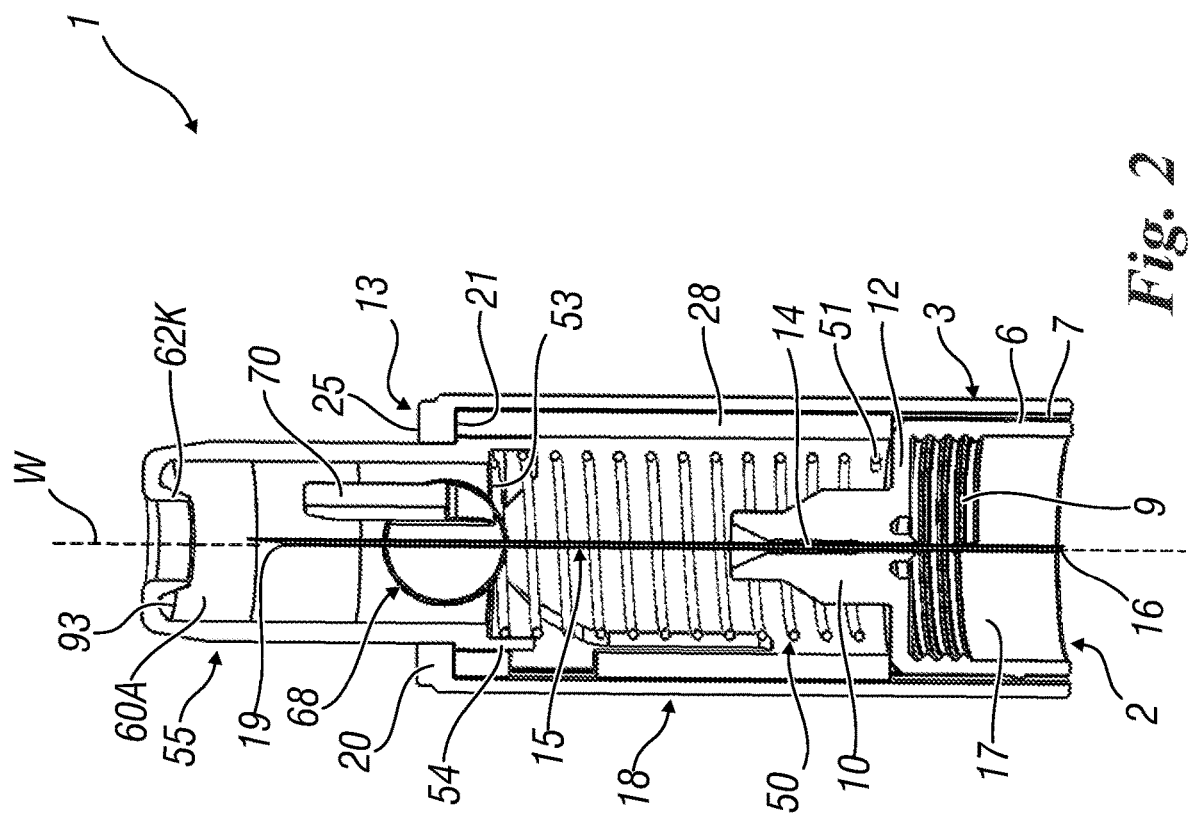

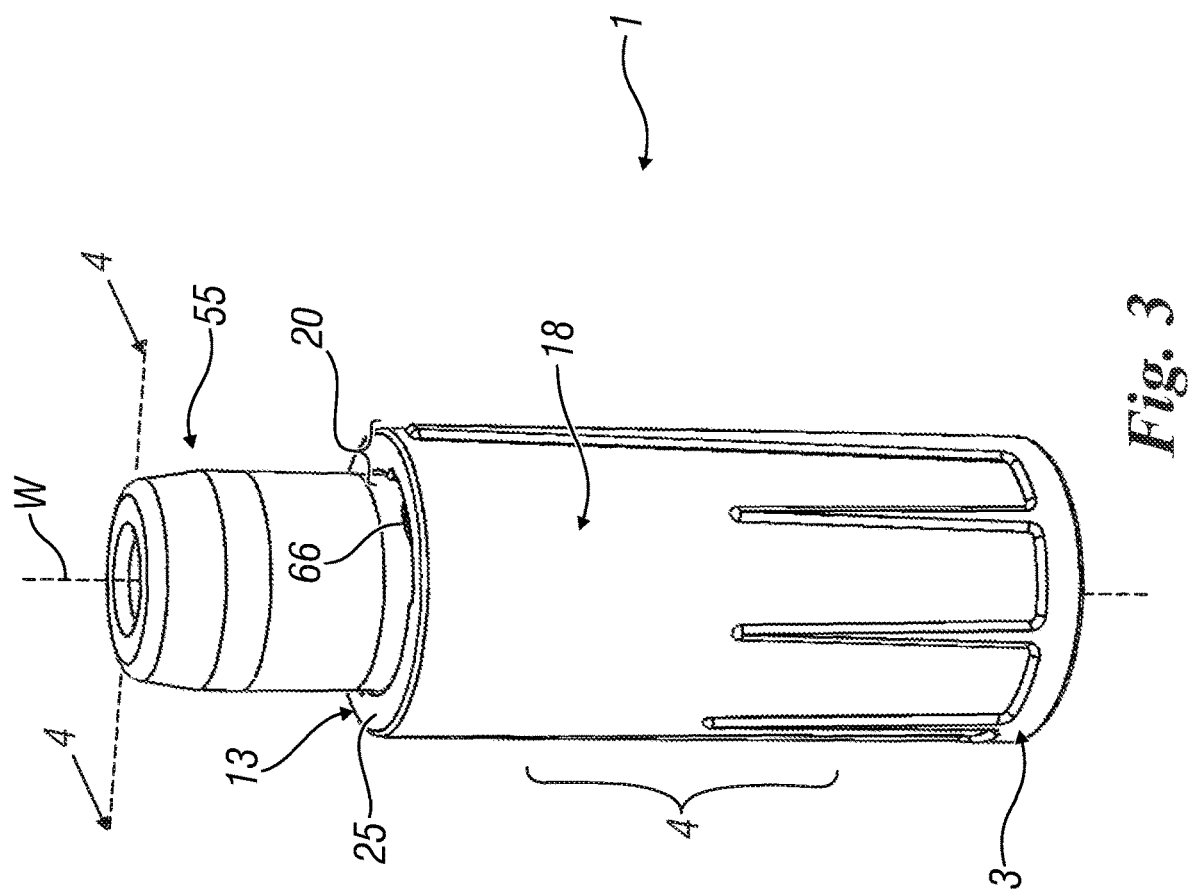

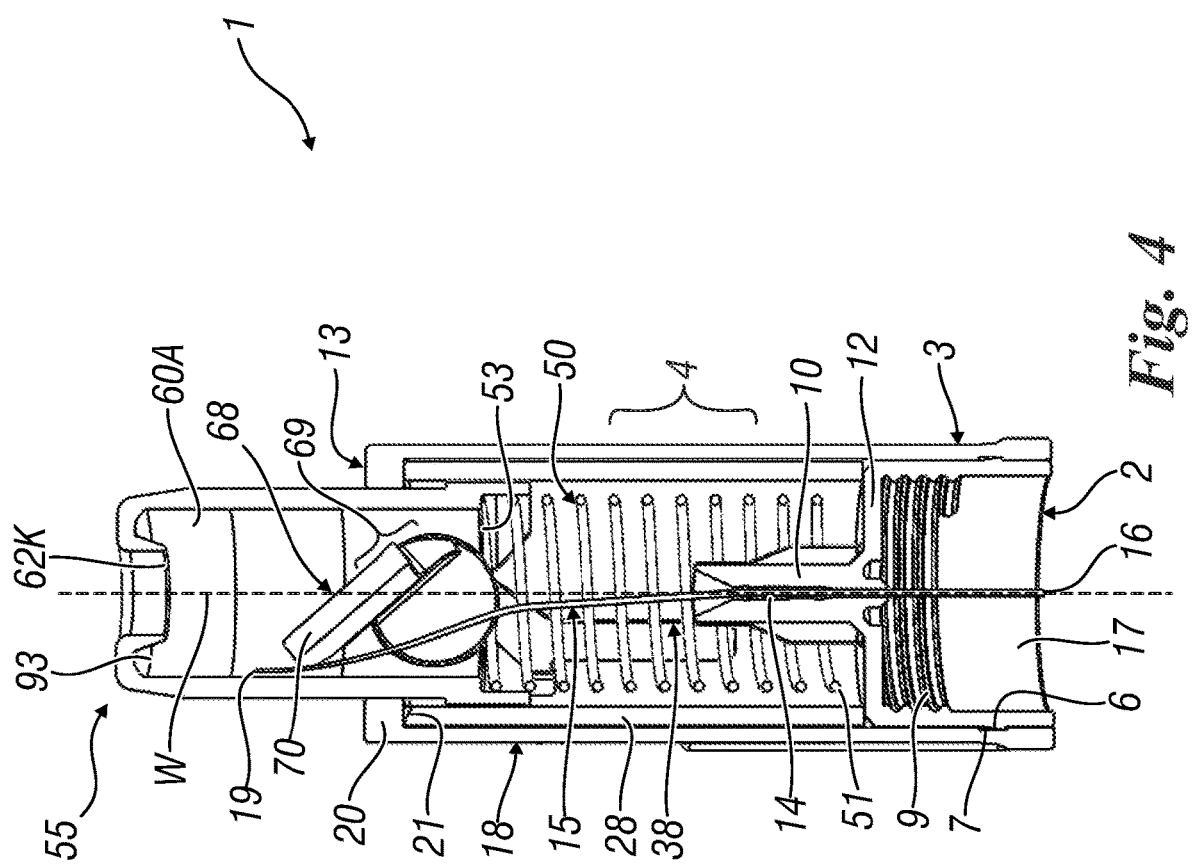

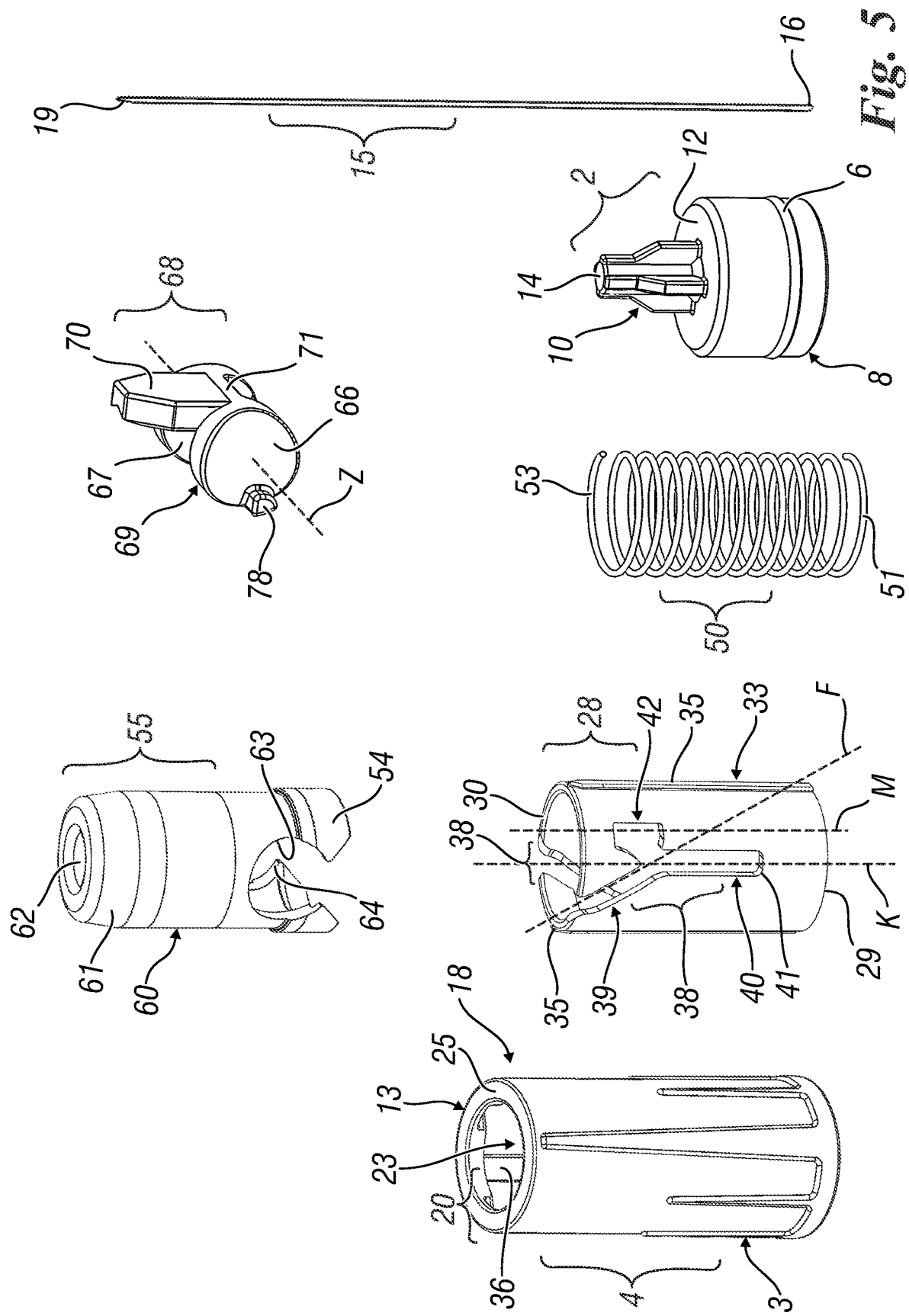

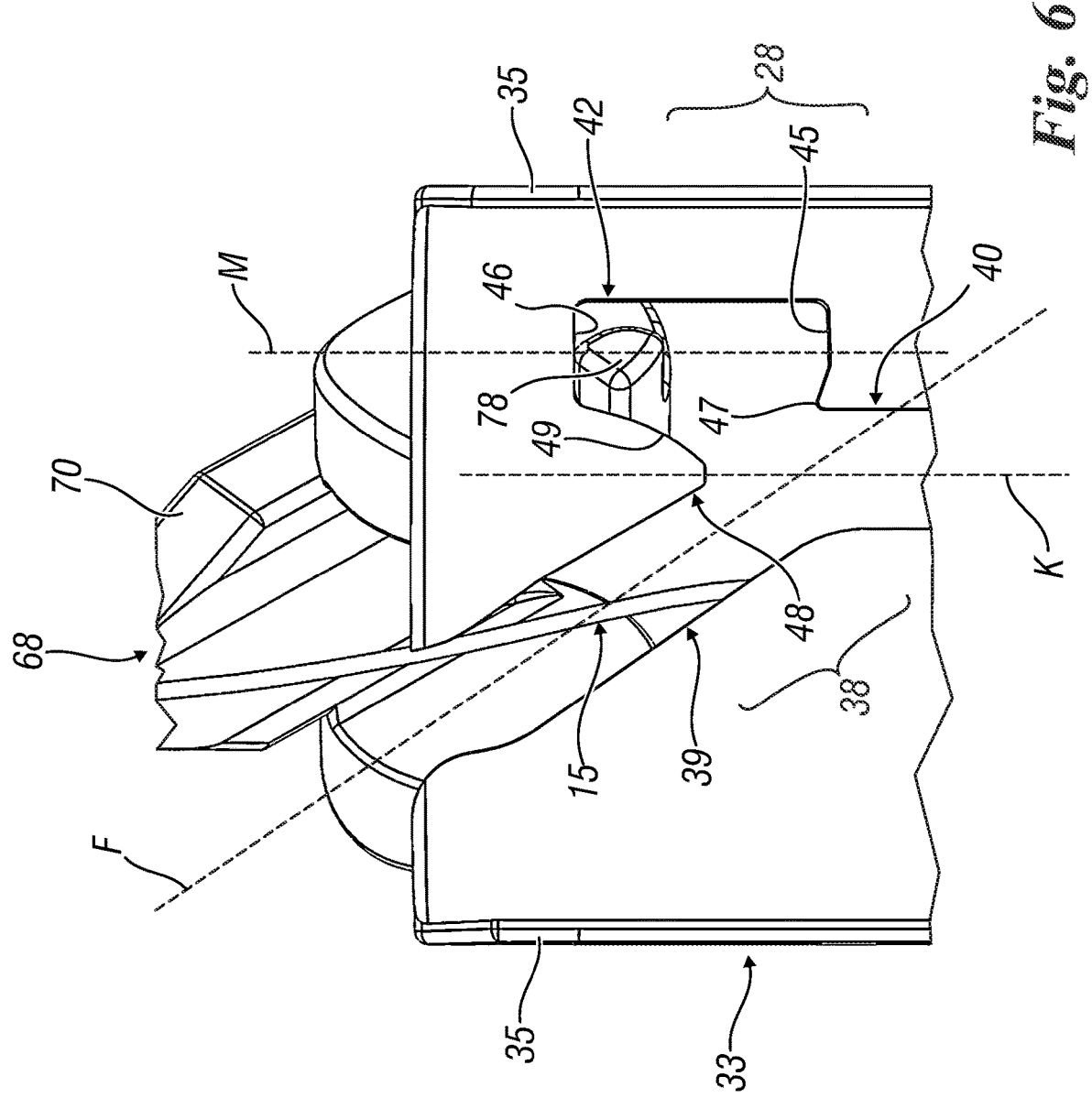

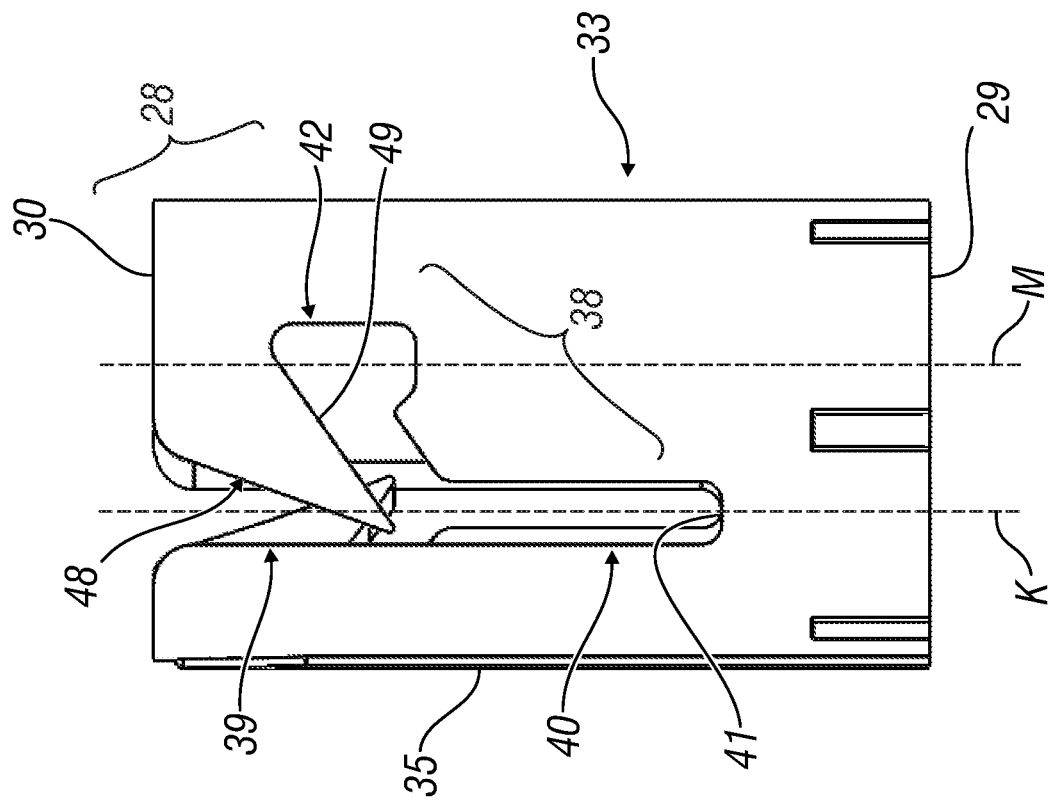

SAFETY NEEDLE WITH DEFORMABLE CANNULA FOR INJECTOR PEN

CROSS-REFERENCE TO RELATED APPLICATIONS

This application is a 371 of PCT/IB2018/053812, filed May 29, 2018, which claims the benefit of Italian Patent Application No. 102017000059104, filed May 30, 2017.

FIELD OF THE INVENTION

The present invention relates to a safety needle according to the precharacterising clause of claim 1.

BACKGROUND OF THE INVENTION

As is known, safety needles, which are also known as safety pen needles, are used together with injector pens for administering drugs to patients. In general, a safety pen needle or simply a safety needle makes provision for a body containing a cannula through which a drug is administered to a patient. The cannula has two ends or extremities: the first end or extremity is distal with respect to the injector pen associated with the needle and is referred to as the "patient side end" or "patient end". During use, this extremity of the cannula penetrates the patient's skin and the drug is administered through it.

The second extremity or end of the cannula is proximal to the injector pen; this is called the "vial side end" or "vial end" because it penetrates a normal rubber septum of the bottle of drug contained within the injector pen.

The injector pen is removably attached to the safety needle, for example, by means of a normal screw coupling between the threaded parts of the safety needle and the injector pen (or other suitable coupling according to current regulations). More particularly, the safety pen usually comprises a plastics component which is connected to the injector pen, the said component supporting both the cannula described above and defining the cannula holder.

Like all cutting devices which come into contact with the human body, use of a pen needle or safety pen presents a problem in view of the fact that it may be a vehicle for the transmission of infectious diseases (such as AIDS, hepatitis and the like) if the needle or better its patient end has to come into contact with health workers assisting the patient in performing administration of the drug or who administer the drug directly to the patient.

Safety needles comprising solutions capable of reducing the risk of accidental punctures and preventing reuse of the needle after administration of the drug are known.

For example, it is known that a moving plastics component associated with the body or rigid structure of the safety needle and actuated by a spring present in such body, at least at the patient end of the cannula, is known. Through its movement this moving component on the one hand allows the drug to be administered by releasing the patient end which can then penetrate the user's skin, and on the other hand acts as a shield against contact with such patient end after such administration has been performed. This is through return to a position which completely covers such patient end and immobilises it in this final position, for example, by suitable projecting plastics members presented by a moving element or by the body of the safety needle which prevent further movement of such protective member or shield capable of again releasing the patient end of the cannula.

Solutions providing for permanent plastic deformation of the cannula after use, and in particular permanent deformation of the cannula at the patient end in such a way that the latter remains permanently and safely within the body of the safety needle or moving element acting as a shield for the patient end, are known. Examples of these solutions are described in US2012/0022461, US2014/0221924, GB2532795. These solutions, such as in general yet others known in the state of the art which however provide protection for the patient end without deformation of the cannula comprise a safety mechanism of the passive type capable of acting to prevent the patient end of the cannula from being exposed to the contact after the safety needle has been used, the said mechanism being automatically activated during and after normal use of the safety needle and not requiring any particular additional operations on the part of the user to protect the aforesaid patient end.

In general, the aforesaid passive safety mechanisms available on the market all operate in a substantially similar way: once the pen needle has been mounted on an injector pen and the usual primary container acting as a protective enclosure together with a sealing element for sterility has been removed, the needle is ready for use. As mentioned, this needle usually has a plastics component which can move relative to the patient end of the cannula, and during use such protective component or element moves relatively with respect to the body of the safety needle, exposing the cannula from the patient end thanks to the thrust reaction which the user exerts against the skin at the point of injection.

While the protective element moves towards the rigid body of the safety needle, the cannula penetrates the skin to its entire useful length so as to administer a drug to the user's subcutaneous adipose tissue (or in any event within the patient's body, whatever the nature of the injection performed, whether subcutaneous, intramuscular or intradermal).

Once it has reached the desired depth at the point of injection and subsequent to delivery of the drug, the user extracts the needle from the point of injection and during such operation the protective element continuously covers the cannula or better its patient end. Once extraction of the protective element is complete, it is, as mentioned, irreversibly immobilised in a position which no longer allows access to the patient end of the cannula. At this point the pen needle or safety needle is removed from the injector and thrown away into suitable containers.

As mentioned, known solutions also provide for elements which deform the cannula after use so that it is safely unable to leave the protective element even if its movement is not immobilised with respect to the body of the safety needle.

In particular, US2014/0221924, which constitutes the precharacterising clause of claim 1 of this document, provides a moving protective element within which a rigid body or fixed sleeve is, for example, screwed onto a cannula holder hub. The protective element is subject to the force of a first spring which bears on the cannula holder hub.

This protective element has two sections having different diameters, a needle disabler element connected to its own support and stressed in rotation with respect to such support by a second torsional spring, preloaded in a predefined angular position before the said disabler element is activated, being located in the section of larger diameter.

The support for this disabler element is located in a first guide slot made in the protective element.

The disabler element comprises a channel which contains the passing needle and engages it in a condition of slight friction to prevent movement of the disabler mechanism with respect to the needle prior to use.

The protective element comprises a first and a second guide slot having a distal section in which the disabler element is positioned before the device mentioned in US2014/0221924 is used, the said distal section being of a width which is smaller than that of a proximal section of the said slot. The width of the distal section is less than that of the proximal section.

During use of the aforesaid device, when the element protecting the cannula penetrates within the sleeve as an injection is being performed, the disabler element moves with respect to the cannula such that it is pressed by such protective element towards the cannula hub; this disabling element, initially present in the distal section of the second guide slot, thus reaches the proximal section of such guide slot.

When injection has been completed, under the thrust of the first spring the protective element moves away from the cannula hub and the supporting element for the disabler element comes into contact with a stop provided in the sleeve, which immobilises such support in the first guide slot. However the protective element continues to move away from the cannula hub, pushed by the first spring, and the disabling element moves into the proximal section of the second guide slot. Because this is wider than the disabling element, such element can rotate under the action of the second spring associated with the support, bending the cannula.

The known solution has a notable construction difficulty, above all associated with the presence of the preloaded spring associated with the supporting element for the disabling element and the presence of the channel containing the needle. These solutions make it difficult to construct the known solution through an automated assembly process, an embodiment in which there is a risk of damaging the end of the cannula as it is inserted into the channel of the disabling element.

In addition to this, the passing connection between the cannula and the disabling element keeps the cannula in a state of stress, which can also create microdeformations or microbending of the cannula at the time when the injection is being performed, something which could also give rise to problems for the patient when injecting the drug and when removing the needle from his or her body.

SUMMARY OF THE INVENTION

The object of this invention is therefore to construct and provide a safety needle or safety pen needle which is improved in relation to the known solutions.

In particular, the object of the present invention is to provide a safety needle of the type capable of deforming the cannula after use so as to render it unusable and not merely covered by the protective element, which is safe to use and which makes it possible to prevent contact between a user and such cannula or the patient end of the cannula with certainty.

Another object is that of providing a safety needle which is simple and effective to manufacture, which can be activated by remaining mounted on the injector pen and which does not comprise elements which raise its costs.

Another object is that of providing a safety needle of the above-mentioned type which is of the passive type and which is automatically and safely activated after use of the safety needle.

These and other objects which will be apparent to those skilled in the art are accomplished through a safety needle according to claim 1.

BRIEF DESCRIPTION OF THE DRAWINGS

For a better understanding of the present invention the following drawings are attached purely for exemplary but not limiting purposes, in which:

FIG. 2 shows a cross-section along the line 2-2 in FIG. 1;

FIG. 3 shows a similar view to that in FIG. 1, but with the needle after use;

FIG. 4 shows a cross-section along the line 4-4 in FIG. 3;

FIG. 5 shows an overall view of the components of the safety needle in FIG. 1 illustrated in perspective view;

FIG. 6 shows a magnified view of a detail of the needle after use; and

FIG. 7 shows a variant of a component of the needle in FIG. 1.

DETAILED DESCRIPTION OF THE INVENTION

Figure 1:
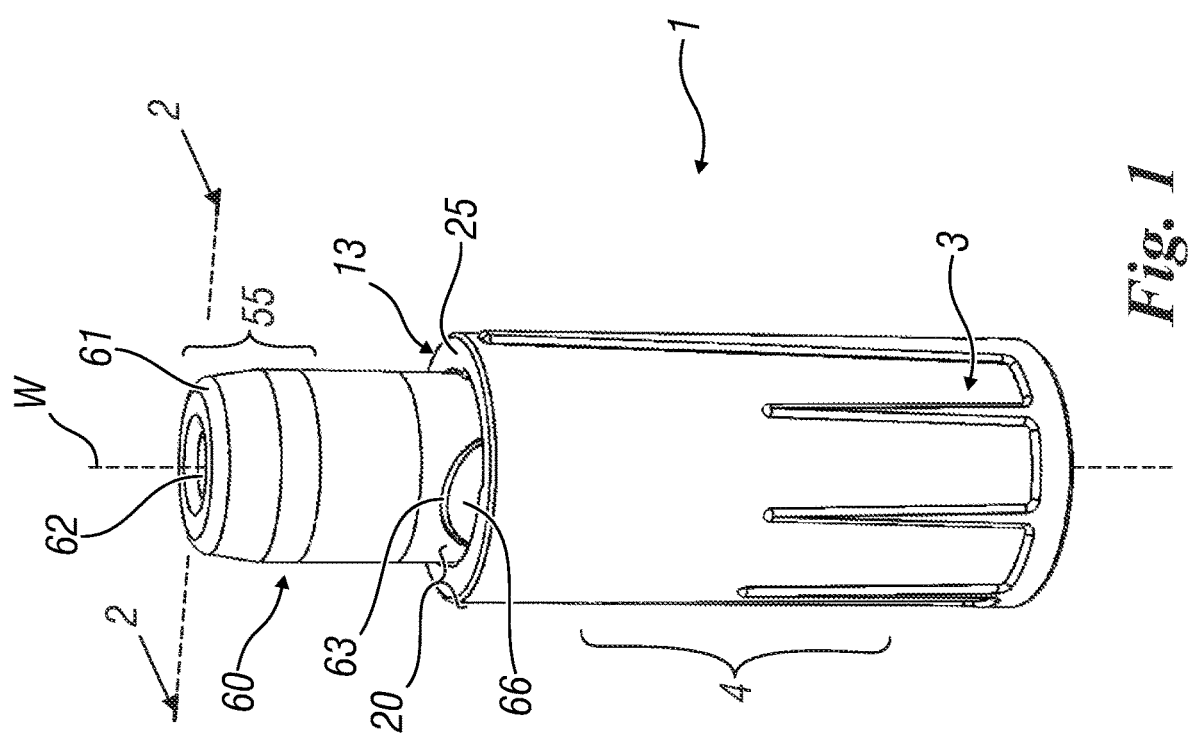
FIG. 1 shows a perspective view of one embodiment of a safety needle according to the invention.

With reference to the figures mentioned, a safety needle (or safety pen needle) according to the invention is generically indicated by 1 and comprises a cannula holder element 2 (or merely "cannula holder") located between a first extremity portion 3 of an outer jacket 4 of needle 1 which is firmly attached in any known way (for example by coupling an outer collar 6 of the cannula holder to an internal recess 7 in the first end portion 3 of outer jacket 4). This outer jacket 4 defines a rigid structure of needle 1.

The cannula has a cup-shaped body 8 and has a threaded internal part 9 whereby body 8 is removably attached to one extremity of a normal injector pen (not shown) for example by screwing (or other suitable coupling). Body 8 of cannula holder 2 has a central part 10 projecting from a transverse portion 12 of cup-shaped body 8 towards the interior of outer jacket 4 and in particular towards second extremity portion 13 of the latter.

Central part 10 has a through axial hole 14 through which there projects a cannula 15 having a first extremity or vial end 16 terminating in internal cavity 17 of cup-shaped body 8 (and able to penetrate a vial of drug associated with the injector pen, also not shown). Cannula 15 is secured within such hole 14 in a known way.

Cannula 15 has a second extremity or patient end 19 capable of penetrating the skin of the patient for subcutaneous administration of the drug contained in the above-mentioned vial.

Outer jacket 4 has a cylindrical body 18, hollow at 23, and partly enclosed by a flat annular part 20 at its second extremity portion 13 (or "distal extremity" of the jacket, considering the position of said extremity portion 13 with respect to the injector pen). Flat part 20 has a first face 21 facing cavity 23 in jacket 4 and a second face 25 facing the exterior of such cavity.

Within outer jacket 4 there is an inner cylindrical sleeve 28 having a first extremity 29 bearing against (or in any event close to) transverse portion 12 of cup-shaped body 8 of cannula holder 2 and a second extremity 30 bearing against (or in any event close to) the first (inner) face 21 of flat part 20 of outer jacket 4. Inner sleeve 28 can be immobilised between outer jacket 4 by part 20 of the latter and cannula holder 2. As an alternative, the inner jacket may be free to rotate within outer jacket 4 about a longitudinal axis W of safety needle 1.

Inner sleeve 28 has a body 33 having at least one external projecting raised surface 35 (two shown by way of example in the figures) capable of being inserted into corresponding longitudinal recesses 36 (or in recesses arranged parallel to the longitudinal axis W of safety needle 1) made internally in outer jacket 4 so as to render them torsionally of one piece with outer jacket 4 and inner sleeve 28. Body 33 has two surface recesses or hollows 38 which, in the example, are through recesses. Obviously such recesses may also be blind or may be simple hollows in the inner surface of sleeve 28.

In a first embodiment each recess 38 is substantially Y-shaped but of a shape having the following characteristics: a first part 39 having a longitudinal axis F lying in a plane which is inclined with respect to above-mentioned W axis, said first part 39 opening towards second extremity 30 of sleeve 28; a second part 40 having a longitudinal axis K lying in a plane at right angles to longitudinal axis W, such second part 40 communicating with the first part without any break in continuity and terminating in a closed extremity 41.

Second part 40 acts together with a third part 42 of recess 38 located on the side of first part 39 and having a longitudinal axis M parallel to the W axis. This third part 42 is slightly offset with respect to the second part, and parallel thereto, and has first and second closed extremities 45 and 46. Close to first extremity 45, close to the second part of recess 38, there is a step 47, while second closed extremity 46 is at a distance from extremity 30 of sleeve 28.

Between the first and third parts 39 and 42 of the recess there is a projection 48 which is tapered towards second part 40 of recess 38, said projection having a curved side 49 which on one side delimits third part 42 of recess 38. The function of this projection 48 will be described below.

The shape of each recess 38 is not however limited to any specific embodiment. In FIG. 7, in which parts corresponding to those in the figures already described are indicated by the same reference numbers, each recess 38 of body 33 of inner sleeve 28 comprises first part 39 and second part 40, both of which are straight and coaxial; while the third part is always at the side, straight and offset with respect to parts 39 and 40 of the recess. Projection 48 is always tapered, but its side 49 is not curved (as in the embodiment described above) but inclined towards the third part of recess 42. The function of this side 49 is nevertheless the same as the analogous curved side described above.

Obviously other embodiments of recess 38 are possible without altering their function, which will become evident from the following description.

Within inner sleeve 28 there is a compression spring having a first extremity 51 bearing on transverse portion 12 of body 8 of cannula holder 2. Spring 51 has a second extremity 53 inserted into a first enlarged extremity part 54 of an element 55 protecting cannula 15, said protective element being able to move against said spring with respect to outer jacket 4 and inner sleeve 28.

More particularly, protective element 55 has a body 60 which is for example substantially cylindrical (as in the figures), hollow at 60A, having aforesaid extremity part 54 and a second extremity part 61 having a through hole 62 for cannula 15 to emerge from for administration of the drug. This hole is preferably (but not necessarily) turned towards the interior of the protective element forming an overturned edge 62K with body 60 of element 55 to create a recess 93. This edge may also be of shapes which differ from that illustrated in the figures.

Before needle 1 is in use and despite being subject to the thrust of spring 50, protective element 55 is held within outer jacket 4 through the joint action of its first extremity part 54 and the second extremity portion 13 of such jacket 4.

Laterally, the protective element has two opposite holes 63 and 64 (which in the non-limiting example in the figures are open on one side) capable of containing corresponding discoidal lateral parts 66 and 67 (or of a shape in any way corresponding to that of holes 63, 64 and suitable for rotating such parts 66 and 67 in said holes 63, 64) of a deforming member or ratchet 68 having a body 69 and capable of rotating between cavity 60A of said protective element (in which it is inserted) to deform cannula 15, as will be described, and hold it within such protective element 55 after use. Rotation of body 69 takes place through a rotary movement of lateral parts 66 and 67 in holes 63 and 64. This is brought about thanks to edges 78, which project from said lateral parts 66 and 67 and are located eccentrically on such lateral parts, capable of acting together with corresponding recesses 38 described above, their movement within which brings about said rotation.

In addition to this, deforming member or ratchet 68 has a part 70 which is for example flat and projects from a portion 71 interconnecting lateral parts 66 and 67. First projecting part 70 is capable of acting together with cannula 15 to deform it in the protective element after use, all this automatically or passively without intervention by the patient or user. Such part 70 may also have another shape which differs from that described and illustrated in the figures and in any event such as to deform cannula 15.

In use, during the stage of administering the drug, with protective element 55 pressing against the patient's skin, this element retracts within outer jacket 4 and into inner sleeve 28 against the force of spring 50. In this movement ledges 78 run into corresponding recesses 38: initially these ledges move through first and second parts 39 and 40 of the corresponding recess, protective element 55 at the same time retracting into outer jacket 4 and inner sleeve 28 so as to expose patient end 19. The user can thus administer the drug. This movement does not bring about any rotation of part 70 of ratchet 68 towards cannula 15. In fact, thanks to the eccentric position of ledges 78 on said parts 66 and 67, slight rotation of the ratchet may occur during downward movement of the protector, but in a direction causing it to move away from the cannula. This movement is nevertheless limited by the inner wall of the protective element.

As needle 1 is moved away from the user's body (or better as outer jacket 4 moves away from such body) spring 50 exerts a thrust on the protective element which again tends to emerge from outer jacket 4 and inner sleeve 28. This thrust also causes ratchet 68 and ledges 78 of the ratchet to move initially along second part 40 of corresponding recess 38. When the ratchet reaches the extremity of projection 48 it is guided by curved side 49 of such projection into third part 42 of recess 38 which also brings about rotation of the ratchet with respect to protective element 55 (because ledge 78 moves along such curved part and because of the displacement of third part 42 of recess 38 located parallel to the side of second part 40 of the recess). This rotation takes place about an axis Z at right angles to the W axis passing through parts 66 and 67 of ratchet 78.

This brings about a thrust force from projecting part of ratchet 68 onto cannula 15 which is now again covered by protective element 55. This action deforms the cannula (as shown in FIG. 4) in such element 55.

Because third part 42 of each recess 38 is closed at a distance from extremity 30 of inner sleeve 28, the protective element cannot fully emerge from outer jacket 4, while the other extremity 45 and step 47 of recess 42 prevent the protective element from further entering outer jacket 4 and inner sleeve 28. Patient end 19 of cannula 15 is therefore deformed and safely held within said protective element 55. This is also thanks to the presence of hole 62 in such element in recess 93 around overturned edge 62K, which can receive patient end 19 of cannula 15 even if such protective element has become lowered into sleeve 28. Obviously the material (plastics) and the thickness of which protective element 55 is constructed impedes perforation by patient end 19 of cannula 15 when such end comes into contact with the wall of said element 55. It will be noted that deformation of the cannula within protective element 55 may help to or will limit the emergence or splashing of contaminated liquid in the case of accidental repetition of the procedure for purging the safety needle (preparatory to injection) remaining accidentally mounted on the injector pen. In fact, in this circumstance such liquid will remain within overturned edge 62K in recess 93 and can only flow outside this later on (without however being projected by dripping from that recess).

This enables the user to be aware that the needle has already been used and at the same time prevents high velocity projections of contaminated fluid.

The solution described is simple, makes no provision for further resilient elements within the safety needle for movement of ratchet 68 (operating as a passive safety deforming member capable of preventing any possible contact with patient end 19) and which therefore has costs comparable to those of already known needles. This is also because the invention does not use further springs or other specifically provided thrust elements (apart from spring 50) to rotate single ratchet 68, also simplifying automatic assembly. In addition to this the invention makes it possible for the cannula to be deformed, despite the fact that the needle remains mounted on the pen. In addition, and optionally, with it being provided that at least the lateral parts 66 and 67 of ratchet 68 are coloured at least externally, because before the needle is used these are clearly visible at the sides of the needle (see FIG. 1), whereas they are almost invisible after use (see FIG. 3), the user has an immediate perception of whether the safety needle has yet been used or not. All this in favour of safety for the user. Obviously, other means for revealing use of the needle may be provided, such as for example coloured parts of protective element 55 which can be seen before use and are covered after use by outer structure 4 or 4 and 28 of the needle.

This invention has various advantages in comparison with the state of the art, and in particular US 2014/0221924.

First of all, there is only one spring in the safety needle described above, something which has obvious advantages of simplicity of construction and economy in comparison with the known solution. By using only one spring there is optimum action by the deforming organ thanks to the particular combination between the path imposed by inner sleeve 28 on ledges 78 of the deforming member and the fact that these ledges are located eccentrically with respect to the axis of rotation of the deforming member.

In addition to this, according to the present invention the deforming member is not coupled with the cannula, does not move along it, and there is therefore no risk of damaging the end of the cannula when the device is being assembled. This has obvious advantages in terms of assemblability. The device according to the invention may in fact be assembled axially without the end or the outer surface of the cannula being damaged by interaction with the deforming member. Interaction between the cannula and the deforming member only takes place when the cannula has been extracted from the patient. This fact constitutes a functional advantage in comparison with what is described in the state of the art.

Furthermore, the deforming member according to the invention is not coupled to the needle but to the protective element and to inner sleeve 28 (through ledges 78). In this way, the deforming member acts on the cannula only after rotation at the end of the travel imposed by the inner jacket, under the thrust of the single spring present. The advantage that a single spring is used (simple, economical) and that the cannula does not move during injection because the deforming element is not coupled to the needle. In fact, even just by moving on the needle the disabling element used in US 2014/0221924 introduces cannula vibrations/oscillations which may cause a nuisance to the user. This fact constitutes an advantage in comfort of use in comparison with the known solution.

Because also the deforming member is not coupled to the cannula, the latter is not characterised by a single first angular position at the initial moment, as for example described in US 2014/0221924. According to the present invention, initially in the first millimetres of movement of the protective device the deforming member is moderately free to take up a number of angular positions which do not in any event result in such deforming member interacting with the cannula before use (given that the more the corrector moves downwards the more the deforming member is positioned parallel to the axis of the cannula). In fact, thanks to the particular shape of the path provided in the inner jacket, the deforming member is caused to straighten parallel to the cannula, without interacting with the cannula. This avoids movements of the cannula due to the deforming member during insertion into the patient's body.

Finally, thanks to the eccentricity of ledges 78, the force required to move ratchet 68 and deflect the cannula in the deformed position is minimal.

Other embodiments of the invention (such as those which provide for outer jacket 4 and inner sleeve 28 to be a single element forming the outer rigid structure of the needle) are possible in the light of the above description and fall within the scope of the invention defined by the following claims.

The invention claimed is:

1. A safety needle comprising an outer structure within which there is a cannula holder element capable of being movably coupled with an injector pen for a drug, said cannula holder element supporting and holding in a passing manner a cannula having a first extremity and a second extremity suitable for administration of the drug, a protective element having a body associated with a rigid structure having a body and being able to move internally within the rigid structure and axially along a longitudinal axis (W) of the safety needle against a spring so as to be able to expose the second extremity of the cannula for administration of the drug, said protective element being substantially cylindrical and hollow, provided with a hole for passage of the cannula and covering said second extremity of the cannula after administration, a deforming member capable of deforming the cannula after administration of the drug in such a way that the second extremity of such cannula remains within said protective element, said deforming member being associated with said protective element and being capable of rotating independently with respect thereto about an axis (Z) at right angles to said longitudinal axis (W) of the safety needle after administration of the drug, said deforming member having a projecting part capable of contacting the cannula during such rotation such as to deform the cannula towards the protective element and immobilize the cannula within the protective element, the deforming member comprising a body inserted into the cavity of said protective element, wherein the projecting part of said deforming member comes into contact with the cannula only after administration of the drug, said body of the deforming member having a portion which connects to discoidal lateral parts inserted into opposite holes made in the protective element and rotating within the said holes, the said discoidal lateral parts having ledges which project and are inserted within corresponding guide recesses made in the body of the rigid structure in which said protective element is inserted, said guide recesses autonomously and completely guiding movement of the protective element and rotation of the deforming member in said protective element.

2. The safety needle according to claim 1, wherein the said rigid structure in which the protective element is inserted comprises a first cylindrical hollow jacket containing a second cylindrical hollow sleeve, said second sleeve having the guide recesses in which the ledges of the deforming member move.

3. The safety needle according to claim 2, wherein the second sleeve is contained in the first jacket in an immobilised way.

4. The safety needle according to claim 2, wherein each recess comprises a first part, a second part, and a third part, the first part opening at one extremity of the second sleeve, said first part being connected without any break in continuity with the second part of the recess having a longitudinal axis (K) parallel to the longitudinal axis (W) of the safety needle, the third part of said recess located on a side of the first part and having a longitudinal axis (M) parallel to the longitudinal axis (W) of the safety needle and in communication with the second part of the recess, said third part of the recess being offset and parallel with respect to the second part of the recess and being closed at two opposite ends, there being a projection capable of guiding the corresponding ledge of the deforming member moving between the second part of the recess towards the third part of the recess being located between the first and third parts of the recess.

5. The safety needle according to claim 4, wherein there is a projection (47) capable of preventing return of the ledge (78) from the third part of the recess (42) to the second part of the recess (40) between the third part (42) of the recess (38) and the second part (40) of the recess.

6. The safety needle according to claim 1, wherein said projecting part of the deforming member projects from the portion connecting the discoidal lateral parts.

7. The safety needle according to claim 1, wherein the hole in the protective element faces the interior of the body of the protective element, a recess being present between an overturned hole and said body, said overturned hole making it possible to retain any projections of fluid transported by the cannula within the said protective element at the end of administration of the drug within the protective element.

8. The safety needle according to claim 1, wherein visual means for revealing use of the needle are provided.

9. The safety needle according to claim 1, wherein the projecting ledges of the deforming member are located eccentrically on the discoidal parts.

* * * * *